US005861275A

United States Patent [19]
Hansen

[11] Patent Number: 5,861,275
[45] Date of Patent: Jan. 19, 1999

[54] LANTIBIOTIC MUTANTS AND CHIMERAS OF ENHANCED STABILITY AND ACTIVITY, LEADER SEQUENCES THEREFOR, GENES ENCODING THE SAME, AND METHODS OF PRODUCING AND USING THE SAME

[75] Inventor: J. Norman Hansen, Silver Spring, Md.

[73] Assignee: The University of Maryland, College Park, Md.

[21] Appl. No.: 535,494

[22] Filed: Sep. 28, 1995

[51] Int. Cl.⁶ .............................. C12P 21/06; C07K 14/00
[52] U.S. Cl. ........................ 435/69.1; 435/69.7; 530/324; 530/300
[58] Field of Search .................................. 435/69.1, 71.3, 435/172.1, 252.3, 320.1, 69.7; 530/300, 317, 323, 324; 536/23.1, 23.4

[56] References Cited

U.S. PATENT DOCUMENTS

| | | | |
|---|---|---|---|
| 4,597,972 | 7/1986 | Taylor | 426/36 |
| 5,260,271 | 11/1993 | Blackburn et al. | 514/2 |
| 5,516,682 | 5/1996 | Hansen | 435/252.3 |
| 5,594,103 | 1/1997 | De Vos et al. | 530/324 |

OTHER PUBLICATIONS

Banerjee et al. 1988. J. Biol. Chem. 263(19):9508–9514.
Database Caplus, 1991, AN–1992:229556, Kuipers, et al., "Expression of Wild–Type and Mutant Nisin Genes in Lactococcus Lactis".
J. Gen. Appl. Microbiol., vol. 38, pp. 271–278, 1992, Tomoko Araya, et al., "Genetic Evidence That Lactococcus Lactis JCM7638 Produces a Mutated Form of Nisin".
J. Biol. Chem., vol. 267, No. 34, pp. 24340–24346, Dec. 1992, Oscar P. Kuipers, et al., "Engineering Dehydrated Amino Acid Residues in the Antimicrobial Peptide Nisin".
J. Biol. Chem., vol. 267, No. 35, pp. 25078–25085, Dec. 15, 1992, Wei Liu, et al., "Enhancement of the Chemical and Antimicrobial Properties of Subtilin by Site–Directed Mutagenesis".
Database DISSABS, vol. 54, No. 3B, p. 1384, 1992, Wei Liu, et al., "Studies of the Antimicrobial Mechanism of Subtilin by Site–Directed Mutagenesis and Elucidation of Chemical, Physical and Antimicrobial Properties of Nisin".
Appl. Envir. Microbiol., vol. 61, No. 8, pp. 2873–2878, Aug. 1995, Harry S. Rollema, et al., "Improvement of Solubility and Stability of the Antimicrobial Peptide Nisin by Protein Engineering".

Gene, vol. 162, pp. 163–164, Aug. 30, 1995, Helen M. Dodd, et al., "A Cassette Vector for Protein Engineering the Lantibiotic Nisin".
Appl. Envir. Microbiol., vol. 62, pp. 2966–2969, Aug. 1996, W. C. Chan, et al., "Structure–Activity Relationships in the Peptide Antibiotic Nisin: Role of Dehydroalanine 5".
J. Biol. Chem., vol. 270, No. 40, pp. 23533–23539, Oct. 6, 1995, Anu Chakicherla, et al., "Role of the Leader and Structural Regions of Prelantibiotic Peptides as Assessed by Expressing Nisin–Subtilin Chimeras in *Bacillus subtilis* 168, and Characterization of Their Physical, Chemical and Antimicrobiol Properties".
Eur. J. Biochem., vol. 216, pp. 281–291, 1993, Oscar P. Kuipers, et al., "Characterization of the Nisin Gene Cluster nisABTCIPR if Lactococcus Lactics: Requirements of Expression of the nisA and nisI Genes for Development of Immunity".
Gene, vol. 127, pp. 15–21, 1993, Juergen Quant, et al., "Versatile Suicide Vectors Which Allow Direct Selection For Gene Replacement in Gram–Negative Bacteria".
Helena Rintala et al., "Biosynthesis of Nisin in the Subtilin Producer *Bacillus subtilis* ATCC6633", Biotechnology Letters, vol. 15, No. 10, pp. 991–999, Oct. 1993).

*Primary Examiner*—Karen Cochrane Carlson
*Attorney, Agent, or Firm*—Oblon, Spivak, McClelland, Maier & Neustadt, P.C.

[57] ABSTRACT

Nisin-subtilin mutant and chimeric pre-peptides were constructed and expressed in a *Bacillus subtilis* strain that possesses all of the cellular machinery for making subtilin, except for the pre-subtilin gene. The chimera $S_L$-$Nis_{1-11}$-$Sub_{12-32}$ was prepared. This pre-peptide has the subtilin leader sequence ($S_L$), the N-terminal portion of the structural region derived from nisin and the C-terminal portion of the structural region derived from subtilin. This chimera was accurately and efficiently converted to the mature lantibiotic, as demonstrated by a variety of physical and biological activity assays. In contrast, a $S_L$-$Sub_{1-11}$-$Nis_{12-34}$ chimera was processed into a heterogeneous mixture of products, none of which appeared to be the correct chimeric lantibiotic. The mixture did, however, contain an active minor component with a biological activity that exceeded nisin itself.

6 Claims, 8 Drawing Sheets

Nis$_{1-11}$-Sub$_{12-32}$ CHIMERA
```
Bst BI                                              SmaI
GATTCGAAAATCACTCCGCAAATCACTAGTATTTCACTTTGTACACCCGGGTGTGTAACTGGTGCATTG
AspSerLysIleThrProGlnIleThrSerIleSerLeuCysThrProGlyCysValThrGlyAlaLeu
              1   2   3   4   5   6   7   8   9  10 11 12 13 14 15 16

BstEII
CAAACTTGCTTCCTTCAAACACTAACTTGTAACTGCAAAATCTCTAAATAGGTAACCC
GlnThrCysPheLeuGlnThrLeuThrCysAsnCysLysIleSerLysTer
 17 18 19 20 21 22 23 24 25 26 27 28 29 30 31 32
```

MUTAGENIC OLIGONUCLEOTIDES USED TO PRODUCE THE Nis$_{1-11}$-Sub$_{12-32}$ CHIMERA
```
  Eco RI    Bst BI
TGAATTCAGATTCGAAAATCACTCCGCAAATCACTAGT      ---> KLENOW
     KLENOW <-----     GGCGTTTAGTGATCATAAAGTGAAACATGTGGGCCCAACTTCGAAACCA
                                              SmaI      HindIII
```

Sub$_{1-11}$-Nis$_{12-32}$ CHIMERA
```
Bst BI                                              Sma I
GATTCGAAAATCACTCCGCAATGGAAAAGTGAATCACCTTGTACACCCGGGTGTAAAACCGGCGCCCTG
AspSerLysIleThrProGlnTrpLysSerGluSerProCysThrProGlyCysLysThrGlyAlaLeu
              1   2   3   4   5   6   7   8   9  10 11 12 13 14 15 16

BstEII
ATGGGTTGTAACATGAAAACAGCCACGTGTCATTGTAGTATTCACGTAAGCAAATAGGTAACCAAATAGGTAACC
MetGlyCysAsnMetLysThrAlaThrCysHisCysSerIleHisValSerLysTer
 17 18 19 20 21 22 23 24 25 26 27 28 29 30 31 32 33 34
```

MUTAGENIC OLIGONUCLEOTIDES USED TO PRODUCE THE Sub$_{1-11}$-Nis$_{12-32}$ CHIMERA
```
    EcoRI     SmaI
GAGAATTCTATCCCGGGTGTAAAACCGGCGCCCTG
ATGGGTTGTAACATGAAAACAGCCACGTGTCATTGT      ---> KLENOW
    KLENOW <-----   CGGTGCACAGTAACATCATAAGTGCATTCGTTTATCCATTGGGGTTCGAAAGTG
                                                       BstEII    HindIII
```

LANTIBIOTIC MUTANTS AND CHIMERAS OF ENHANCED STABILITY AND ACTIVITY, LEADER SEQUENCES THEREFOR, GENES ENCODING THE SAME, AND METHODS OF PRODUCING AND USING THE SAME

This work was supported by National Institutes of Health grant AI24454. Therefore, the U.S. government may have certain rights in the present invention.

BACKGROUND OF THE INVENTION

1. Field of the Invention

The present invention concerns lantibiotic mutants and chimeras of enhanced stability and activity, leader sequences for such lantibiotic mutants and chimeras, genes encoding such lantibiotic mutants and chimeras (both with and without the leader sequences), and methods of producing and using the same.

2. Discussion of the Background

Nisin (a 34-residue long peptide produced by *Lactococcus lactis*) and subtilin (a 32-residue long peptide produced by *Bacillus subtilis*) are the most thoroughly-studied examples of lantibiotics. Lantibiotics are ribosomally-synthesized antimicrobial peptides characterized by the presence of unusual lanthio and dehydro amino acid residues. The structures of nisin and subtilin are shown in FIG. 1. Their biosynthesis involves several post-translational modifications; e.g., dehydration of serines and threonines, formation of thioether crosslinkages between dehydro residues and cysteines, translocation, removal of a leader sequence, and/ or release of the mature antimicrobial peptide into the extracellular medium (reviewed in refs. 1–3 below).

Gene-encoded antimicrobial peptides constitute a family of natural products whose known members are expanding rapidly in number and diversity, and are produced by many kinds of organisms, ranging from bacteria to eukaryotes, including mammals (1, 4–6). The ubiquity of anti-microbial peptides among widely diverged organisms implies that the peptides have been subject to many different strategies for achieving their antimicrobial properties, some of which are quite different from the properties and corresponding mechanisms of classical antibiotics such as penicillin. It may therefore be possible to supplement the arsenal of therapeutic antimicrobial agents that has been depleted as a result of the evolution of resistance among microbes.

An advantage unique to gene-encoded antimicrobial peptides is that their structures can be readily manipulated by mutagenesis, which provides a facile means for constructing and producing the large numbers of structural analogs needed for structure-function studies and rational design. Whereas this advantage is shared by all gene-encoded antimicrobial peptides, the lantibiotics are unique in possessing the unusual dehydro and lanthio amino acid residues, which are absent from magainins (7–9), defensins (10–13), or cecropins (14, 15). This means that the lantibiotics offer chemical and physical properties, and hence biological activities, that are not attainable by polypeptides that lack these residues.

For example, the dehydro residues (dehydroalanine, or "Dha," and dehydrobutyrine, or "Dhb") are electrophiles, whereas none of the 20 common natural amino acids is electrophilic. The thioether crosslinkages of lantibiotics are more resistant to cleavage or breakage than the more common disulfide bridge of proteins lacking lanthio residues. For example, a thioether crosslinkage can survive reducing conditions and extremes of pH and temperature better than a disulfide bridge (16).

A concern when making mutants of lantibiotics is the effect of the mutations on the post-translational modification process, because a mutation that disrupts processing makes the biosynthesis of the corresponding mature lantibiotic peptide impossible. All known lantibiotic prepeptides contain an N-terminal region that is cleaved during maturation. For the Type A lantibiotics (e.g. nisin, subtilin, epidermin), this leader region is highly conserved (17). Participation of the leader sequence in the orchestration of post-translational modification and secretion has been proposed (17, 18).

Certain mutations in the leader region of the nisin prepeptide have rendered the cell incapable of nisin production (19), whereas many mutations in the structural region of several lantibiotics do not disrupt processing (e.g., U.S. application Ser. No. 07/981,525 and refs. 20 and 21)). When the complete nisin prepeptide consisting of the nisin leader region and the nisin structural region ($N_L$-$Nis_{1-34}$) was expressed in a subtilin-producing cell, no nisin-related peptide products were detectable (22, 23). However, when a chimera consisting of the subtilin leader region and the nisin structural region ($S_L$- $Nis_{1-34}$) was expressed in a subtilin-producing cell, an inactive nisin-like peptide was produced in which the leader region had been correctly cleaved and which contained a full complement of unusual amino acids (22). The lack of activity was attributed to the formation of incorrect thioether crosslinkages (22).

Similarly, when a prepeptide consisting of a subtilin leader region and a nisin structural region was expressed in a nisin-producing cell, the nisin structural region contained the unusual amino acids, but the leader was not cleaved (24). It has also been reported that expression of a prepeptide consisting of the nisin structural region fused to a subtilin-nisin chimeric leader region, $S_{L(1-7)}$-$N_{L(8-23)}$-$Nis_{(1-34)}$, forms active nisin when expressed in a subtilin-producing cell (23).

These results imply that subtilin processing strains such as *B. subtilis* are not capable of recognizing the nisin prepeptide (which is ordinarily expressed in *Lactococcus lactis*) and converting it to nisin. However, the subtilin processing machinery will perform modification reactions on the nisin structural peptide if it is attached to a subtilin leader region, although the modifications seem to be misdirected so that active nisin is not always produced. Finally, the subtilin processing machinery will produce active nisin if the leader region is an appropriate combination of subtilin leader and nisin leader sequences.

Lantibiotics are known to be useful bacteriocides and food preservatives. Methods of producing lantibiotics are also known. Lantibiotics offer the advantages of peptide products, in that they are more easily digested, tolerated and/or secreted by humans, other mammals and other animals which may ingest the same than are some so-called "small molecule" preservatives. Therefore, a need is felt for new lantibiotics having improved chemical, physical and/or biological properties and for improved methods of producing the same.

SUMMARY OF THE INVENTION

The present invention concerns polynucleic acids which encode a chimeric or mutant lantibiotic of the formula:

(leader)–(lantibiotic)

where the leader is selected from the group consisting of the subtilin leader sequence, the nisin leader sequence, and chimeras of said subtilin leader sequence and said nisin leader sequence which permit production of an active lantibiotic in a lantibiotic-producing host, and the lantibiotic is a mutant or chimeric lantibiotic, preferably of subtilin and/or nisin; vectors and plasmids containing the same; transformants containing the same, capable of expressing a prepeptide and/or biologically active peptide from the same; prepeptides encoded by the polynucleic acids; biologically active peptides expressed and/or processed by lantibiotic-producing hosts; methods of making the polynucleic acids, vectors, plasmids, prepeptides and biologically active peptides; and methods of using the same.

BRIEF DESCRIPTION OF THE DRAWINGS

FIG. 2 shows a strategy for construction of nisin-subtilin chimeras;

DETAILED DESCRIPTION OF THE INVENTION

Figure 1:
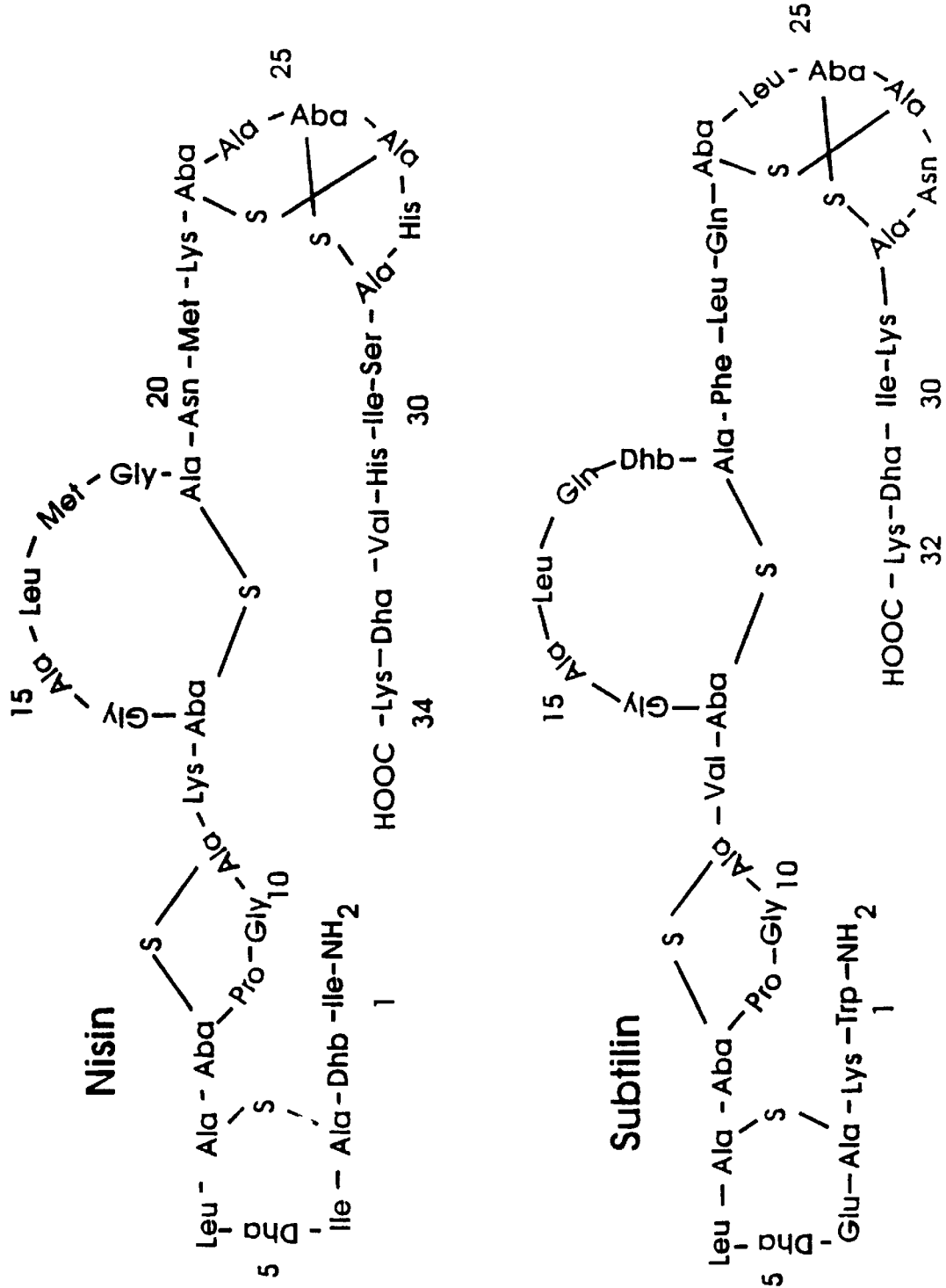
FIG. 1 shows the structures of nisin (SEQ ID NO:1) and subtilin (SEQ ID NO:2) as determined by Gross and co-workers (37–39); the unusual amino acids Aba (aminobutyric acid), Dha (dehydroalanine), Dhb (dehydrobutyrine or β-methyldehydroalanine), Ala-S-Ala (lanthionine) and Aba-S-Ala (β-methyllanthionine) were introduced by post-translational modifications as described hereinbelow.

The present invention explores the contribution of the structural region and its relationship to the leader region by the construction and expression of nisin-subtilin chimeras which contain chimeric nisin-subtilin structural regions fused to the subtilin leader region. The present inventors have discovered that chimeras in which the C-terminal portion of the structural region correspond to subtilin are processed correctly and give active products, whereas those in which the C-terminal portion of the structural region corresponds to nisin produces a heterogeneous mixture of products, most of which, but not all, are inactive.

The phrase "polynucleic acid" refers to RNA or DNA, as well as mRNA and cDNA corresponding to or complementary to the RNA or DNA isolated from a lantibiotic-producing host. The term "gene" refers to a polynucleic acid which encodes a peptide, prepeptide, protein or marker, or to a vector or plasmid containing such a polynucleic acid.

In the present application, a "chimera" refers to a peptide or protein in which the amino acid sequence is taken in part from a first peptide or protein, and in part from a second, distinct protein or peptide. A "mutant" gene or peptide refers to a gene or peptide having a sequence which differs from the corresponding naturally-occurring sequence in that one or more bases or residues are deleted, substituted or added at any position therein, including either terminus.

In the present application, the following formulaic indicators have the following meanings:

| | |
|---|---|
| $S_L$: | the subtilin leader sequence |
| $S_{L(x-y)}$: | the subtilin leader sequence from position x to position y |
| $N_L$: | the nisin leader sequence |
| $N_{L(x-y)}$: | the nisin leader sequence from position x to position y |
| $Sub_{x-y}$: | the sequence of the subtilin peptide from position x to position y |
| $Nis_{x-y}$: | the sequence of the nisin peptide from position x to position y |

In the context of the present application, the chimera "$Nis_{1-4}Sub_{5-32}$" is the same as the chimera "$Nis_{1-11}Sub_{12-32}$" since the amino acids at positions 5–11 of both nisin and subtilin are identical. Thus, for example, "$Nis_{1-7}Sub_{8-32}$" is the same as each of $Nis_{1-4}Sub_{5-32}$ and $Nis_{1-11}Sub_{12-32}$.

The "lantibiotic processing machinery" refers to the metabolic events occurring in a lantibiotic-producing microorganism which result in processing and formation of the lantibiotic. For example, the "subtilin processing machinery" and the "nisin processing machinery" refer to those metabolic processes and events occurring, respectively, in a subtilin-producing microorganism which result in the processing and/or formation of subtilin, and in a nisin-producing microorganism which result in the processing and/or formation of nisin.

Naturally-occurring nisin and subtilin, leader sequences and genes encoding the same are disclosed in U.S. application Ser. No. 07/214,959, now U.S. Pat. No. 5,218,101, incorporated herein by reference in its entirety. Subtilin mutants and methods of producing and using the same are described in U.S. application Ser. Nos. 07/981,525 and 08/220,033, each of which is incorporated herein by reference in their entireties.

In the present application, "biological activity" preferably refers to activity against *Bacillus cereus* spores and/or vegetative cells. Preferably, biological activity against *Bacillus cereus* spores is measured using the "halo assay" described in the experimental section hereunder, and biological activity against *Bacillus cereus* vegetative cells is measured using the liquid culture assay described in the experimental section hereunder.

The present invention concerns polynucleic acids which encode a chimeric or mutant lantibiotic of the formula:

(leader)–(lantibiotic)

where the leader is selected from the group consisting of the subtilin leader sequence, the nisin leader sequence, and chimeras of said subtilin leader sequence and said nisin leader sequence which permit production of an active lantibiotic in a lantibiotic-producing host, and the lantibiotic is a mutant or chimeric lantibiotic, preferably of subtilin and/or nisin;

subject to the proviso that when the lantibiotic is a mutant subtilin in which the 4-position of native subtilin as shown in FIG. 1 is substituted with isoleucine and in which the 5-position may be substituted with alanine, the leader is not the subtilin leader sequence.

The present polynucleic acid may encode a chimeric leader sequence of the formula:

$S_{L(1-x)}$-$N_{L([x+1]-23)}$ or $N_{L(1-x)}$-$S_{L([x+1]-23)}$

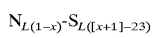

where x is a number of from 1 to 22, selected such that the lantibiotic processing machinery of a lantibiotic-producing host transformed with the present gene produces either a biologically active lantibiotic or a prepeptide which can be converted to a biologically active lantibiotic using the lantibiotic processing machinery of an appropriate lantibiotic-producing host. (When x is 1, "1–x" becomes 1, and when x is 22, "[x+1]–23" becomes 23.) When a chimeric leader is used, x is preferably from 5–18, more preferably from 6–15, and most preferably, the chimeric leader is $S_{L(1-7)}$-$N_{L(8-23)}$.

However, the present polynucleic acid preferably encodes a naturally-occurring lantibiotic leader sequence, such as $S_L$ or $N_L$.

Preferably, the lantibiotic-producing host transformed with the present polynucleic acid is a subtilin-producing host or a nisin-producing host. More preferably, the subtilin-producing host is a strain of *Bacillus subtilis*, such as *B. subtilis* 6633 or *B. subtilis* 168, and the nisin-producing host is a strain of *Lactobacillus lactis*, such as *L. lactis* 11454. Most preferably, when a subtilin-producing host is used to produce or express the present peptide or prepeptide, the polynucleic acid encodes either the $S_L$ leader sequence or a $S_{L(1-x)}$-$N_{L([x+1]-23)}$ chimeric sequence where x is 7, and when a nisin-producing host is used to produce or express the present peptide or prepeptide, the polynucleic acid encodes the $N_L$ leader sequence.

Preferably, the lantibiotic encoded by the present gene and processed by a lantibiotic-producing host is one of the formula:

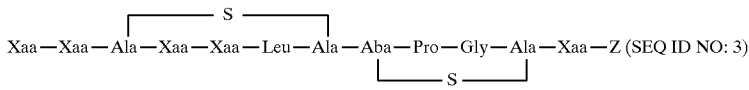

Xaa—Xaa—Ala—Xaa—Xaa—Leu—Ala—Aba—Pro—Gly—Ala—Xaa—Z (SEQ ID NO: 3)

where Xaa is any amino acid, including a dehydro amino acid residue or one of the two residues of a lanthio amino acid as defined herein, and Z is either $Nis_{13-34}$ or $Sub_{13-32}$, with the proviso that when Z is $Sub_{13-32}$, then, simultaneously, the 1-position is not Trp, the 2-position is not Lys, the 4-position position is not Ile, and the 5-position is not Dha or Ala.

Preferred residues at the 1-position include Trp and Ile; at the 2-position include Lys and Dhb; at the 4-position include Ile; at the 5-position include Dha and Ala; and at the 12-position include Val and Lys; and conservatively substituted forms thereof. An amino acid residue in a protein, polypeptide, or prepeptide is conservatively substituted if it is replaced with a member of its polarity group as defined below:

Basic amino acids:
lysine (Lys), arginine (Arg), histidine (His)
Acidic amino acids:
aspartic acid (Asp), glutamic acid (Glu), asparagine (Asn), glutamine (Gln)
Hydrophilic, nonionic amino acids:
serine (Ser), threonine (Thr), cysteine (Cys), asparagine (Asn), glutamine (Gln)
Sulfur-containing amino acids:
cysteine (Cys), methionine (Met)
Aromatic amino acids:
phenylalanine (Phe), tyrosine (Tyr), tryptophan (Trp)
Hydrophobic nonaromatic amino acids:
glycine (Gly), alanine (Ala), valine (Val), leucine (Leu), isoleucine (Ile), proline (Pro)
Dehydro amino acids:
dehydroalanine (Dha), dehydrobutyrine (Dhb)
Lanthio amino acids:
lanthionine (Ala-S-Ala), β-methyllanthionine (Aba-S-Ala), β,β'-dimethyllanthionine (Aba-S-Aba)

Particularly preferred residues at the 1-position include Trp and Ile; at the 2-position include Lys and Dhb; at the 4-position include Ile; at the 5-position include Dha; and at the 12-position include Val and Lys.

Based on the experimental results described herein, it is expected that any amino acid can exist at positions 1, 2, 4 and 12 of the mature lantibiotic, and a biologically active peptide can be produced. The procedures described herein easily enable one to produce any such mutant or chimeric peptide, then test its biological activity against *B. cereus* spores and/or cells. As one can easily tell in comparing the sequences of mature nisin and mature subtilin, the differences at positions 1, 2, 4 and 12 are a result of non-conservative substitutions. Thus, it appears that the specific identities of the residues in the native proteins may not be essential to maintaining a high degree of biological activity, and any amino acid residue at any one of these positions, particularly where the activity is the same as or equal to that of subtilin or nisin, is expected to be producible and useful. (Naturally-occurring nisin and subtilin, and polynucleic acids encoding the same, are excluded from the scope of the present invention.)

The present invention also concerns an expression vector, plasmid and transformant comprising the present polynucleic acid. In preferred embodiments, the expression vector is one in which the present polynucleic acid is inserted into the BstEII-BstEII site of the plasmid pSMcat (deposited under the terms of the Budapest Treaty at the American Type Culture Collection, Rockville, Md. 20852, U.S.A., under Designation No. 75914; also see Ser. No. 07/981,525) or the SpeI-BstEII site of pACcat (see the description below).

The present invention also concerns a method of producing a polynucleotide encoding a mutant or chimeric lantibiotic prepeptide, comprising (A) replacing a native gene encoding a lantibiotic with a gene consisting essentially of a selective marker, such that a lantibiotic-producing host in which the native lantibiotic gene is replaced is unable to produce the lantibiotic (as determined by a halo or liquid culture assay), and (B) subsequently replacing the selective marker with a polynucleic acid encoding the mutant or chimeric lantibiotic. The polynucleotide encoding a mutant or chimeric lantibiotic prepeptide may be in the form of a vector or plasmid, which may have appropriate sequences and an appropriate construction to express the mutant or chimeric peptide or prepeptide.

When a suitable lantibiotic-producing host is transformed with the polynucleotide encoding the mutant or chimeric lantibiotic prepeptide, only the mutant or chimeric lantibiotic is produced in significant amounts by the transformant.

Some or all mutant or chimeric lantibiotics produced by such transformants are expected to exhibit biological activity. The mutant or chimeric lantibiotic produced by the present method preferably has a biological activity (as defined above) equal to or greater than that of nisin, more preferably, at least twice that of nisin, and may even have a biological activity of from 4 times to 35 times that of nisin (see the experimental section below). The mutant or chimeric lantibiotics produced by such transformants may also exhibit improved chemical stability, as measured by the disappearance of the signals of the vinylic protons of the dehydro residues in $^1$H NMR spectra as a function of time. Preferably, the mutant or chimeric lantibiotics produced by the present method and/or transformants exhibit a half-life of at least 48 days, more preferably at least 72 days, and most preferably, a half-life which cannot be determined by $^1$H NMR spectroscopy after 72 days incubation in the dark in aqueous solution.

The present method of producing a mutant or chimeric lantibiotic also involves the step of culturing a lantibiotic-producing host transformed with the present polynucleic acid, vector or plasmid in a suitable medium, and recovering the lantibiotic from the culture medium. Culturing is generally performed for a length of time sufficient for the transformant to produce, process and/or secrete the mutant or chimeric peptide. A "suitable" medium is one in which the lantibiotic-producing microorganism grows and produces the lantibiotic peptide or prepeptide. This method may also include the step of rupturing or lysing the transformed cells prior to recovering the lantibiotic. Alternatively, the cells of the transformed host may be recovered and recultured.

Continuous processes for producing the present lantibiotic are also envisioned, comprising the additional steps of withdrawing the culture medium continuously or intermittently, separating the transformant from the withdrawn culture medium, recirculating the separated transformant to the culture vessel, and recovering the lantibiotic from the withdrawn culture medium from which the transformant has been separated.

The present invention also concerns a method of treating, killing or inhibiting the growth of microorganisms and/or spores thereof, comprising contacting a microorganism, spore thereof or a medium subject to infection or infestation by said microorganism or spore, with an effective amount or concentration of the present lantibiotic mutant or chimera. In this context, microorganisms and/or spores to be treated by this method are those which are killed or whose growth is inhibited by a lantibiotic. An "effective amount or concentration" refers to an amount or concentration which kills or inhibits the growth of the microorganism or spore.

Any use for which nisin, subtilin or other known lantibiotics are used are also envisioned for the present lantibiotic. For example, a medium which can be treated by this method may be a food product or a substance which is used in making food products. Furthermore, the medium may be an inert carrier, and such a composition may be used in a conventional manner as a bacteriocide.

Other features of the invention will become apparent in the course of the following descriptions of exemplary embodiments which are given for illustration of the invention and are not intended to be limiting thereof.

EXAMPLES

Bacterial strains, cloning vectors, and mutagenesis. *Bacillus subtilis* 168 strains and cloning vectors used were LHermΔS (deposited under the terms of the Budapest Treaty at the American Type Culture Collection, Rockville, Md. 20852, U.S.A., under the ATCC Designation No. 55625; see also U.S. application Ser. No. 07/981,525 and ref. 21), pTZ19U (Life Technologies, Gaithersberg Md.), pSMcat (see U.S. application No. 07/981,525 and ref. 21), and pACcat (this work). Structural mutants of subtilin were constructed and expressed using the cassette mutagenesis system previously described in U.S. application Ser. No. 07/981,525 (also see ref. 21). Cloning vector pACcat was constructed by replacing the upstream BstEII site in the plasmid pSMcat with an SpeI site by mutagenesis, thus making the downstream BstEII site a unique site.

Synthetic oligonucleotides were annealed, filled in using Klenow fragment, restricted with EcoRI and HindIII and cloned into the EcoRI-HindIII site of pTZ19U. The cloned fragment, which contained the mutation, was cut out with appropriate restriction enzymes and cloned into the corresponding site of the pSMcat vector or the pACcat vector. The mutated sequence was confirmed by sequence analysis of the cloned insert using the SEQUENASE version 2.0 sequencing kit from United States Biochemicals (Cleveland, Ohio.). This mutant gene was introduced into the chromosome of LHermfΔS (from which the natural subtilin gene had been deleted) by transformation and Campbell-type integration using selection on chloramphenicol plates (21).

Culture conditions and purification of chimeric peptides. Strains producing the mutant peptides were grown in Medium A (21, 25), modified to contain 2% sucrose and 10 μg/mL chloramphenicol. The culture was incubated with vigorous aeration for 25–35 hr at 35° C., acidified to pH 2.5 with phosphoric acid and heated to 121° C. for 3 min to inactivate proteases. A 0.5 part by volume of n-butanol (relative to 1 part by volume of culture) was added. The mixture was stirred at 4° C. for 2 h, allowed to stand at 4° C. for 2 h, and centrifuged. Acetone (2.5 parts by volume, relative to 1 part by volume of the mixture) was added to the supernatant, and the resultant mixture allowed to stand at −20° C. for 16 h, and centrifuged. The pellet was lyophilized and resuspended in 20% acetonitrile with 0.05% trifluoroacetic acid. This suspension was immediately purified on a C-18 reverse-phase-HPLC column using a trifluoroacetic acid (0.05%)-water-acetonitrile gradient in which the acetonitrile varied from 0 to 100% over 30 min at a rate of 1.2 mL/min, unless indicated otherwise.

NMR and mass spectral analyses. Samples for $^1$H NMR spectral analysis were dissolved in deuterated water (99.96 atom % D, Aldrich Chemical Co.), lyophilized (repeated twice) to exchange protons and dissolved in $D_2O$ to a final concentration of 2–3 mg/mL. $^1$H NMR spectra were obtained using a Bruker AMX-500 spectrometer interfaced to an Aspect 3000 computer. Spectra were obtained at a constant temperature of 295K, using selective solvent suppression. Data were processed using UXNMR software. Mass spectral analysis was performed by PeptidoGenic Research & Co. (Livermore, Calif.) on a Sciex API I Electrospray Mass Spectrometer which has an analysis range of over 200,000 Da with +/−0.01% accuracy, on 5 μL samples at a concentration of about 5 pmol/μL. The reported masses are those calculated as the most probable values based on the different m/z forms.

Measurement of biological activity. Biological activity was measured using an inhibition zone (halo) assay (ref. 21 and U.S. application Ser. No. 07/981,525) and a liquid culture assay (26). HPLC fractions were tested for activity by spotting 15 μL onto an agar plate (modified Medium A), incubating at 37° C. for 15 min., spraying with *B. cereus* T spores and incubating at 37° C. for 16 hr. Positive inhibition is defined as and was determined by a clear zone containing spores that were inhibited during outgrowth surrounded by an opaque lawn of cells derived from the spores that had become vegetative.

In the liquid culture assay, various concentrations of peptide were added to a suspension of *B. cereus* T spores in modified medium A and incubated in a rotating drum shaker at 30° C. for 90 min. The inhibitory effects were evaluated using phase contrast microscopy and a Klett-Summerson calorimeter. After incubation, cells were viewed by phase-contrast microscopy to determine their stage of outgrowth. Those cells in early stages of outgrowth (phase-dark and swollen, but only slightly elongated) were considered inhibited. Those cells that were fully elongated and/or divided were considered to be not inhibited. The inhibitory concentration is the concentration of peptide which arrests a majority of the population of spores at the stage of early outgrowth after the 90-min incubation period. Further, spore germination and outgrowth are accompanied by known changes in the optical density at 650 nm. Thus, the stage of outgrowth can be monitored and the inhibitory concentration can be confirmed using a Klett-Summerson colorimeter. Definitive determinations of the inhibitory concentration of peptide advantageously employ both phase-contrast microscopy and measurement of the optical density at 650 nm.

Relative amounts of peptide were also estimated by integration of peak areas (measured at 214 nm) of the HPLC profiles, using nisin as a standard. It was assumed that the extinction coefficients of the mutant peptides are the same as nisin at this wavelength.

The activity of the chimeric $Nis_{1-11}$-$Sub_{12-32}$ peptide towards inhibiting *B. cereus* vegetative cells was also determined. Heat-shocked *B. cereus* T spores (150 micrograms) were added to 1% tryptone (Difco)–0.1M Tris-phosphate buffer (2 ml) at pH 6.8. The mixture was incubated for 2 hours at 37° C. in a rotating drum shaker, whereupon all of the spores were in the vegetative state. The chimeric peptide was then added, and incubation was continued for one additional hour. Cell lysis was monitored by turbity (measured in Klett units), and the integrity of the cell was determined by phase-contrast microscopy. Relative inhibitory effectiveness was measured as the amount of inhibitory peptide required to reduce the turbity by 50%.

SDS-PAGE analysis. The sizes of the peptides were estimated using TRICINE-sodium dodecylsulfate polyacrylamide gel electrophoresis, designed for proteins in the range of from 1 to 100 kD (27), using a 4% stacking gel, a 10% spacer gel, and a 16.5% separating gel. Gels were silver-stained using KIT #161-0443 from Bio-Rad (Richmond, Calif.) according to manufacturer's instructions.

RESULTS

Inspection of the structures of nisin and subtilin (shown in FIG. 1) reveals that the number and locations of the thioether rings and Dha residues are conserved. Each peptide has one Dhb residue, but its position is not conserved. The N-terminal region is relatively conserved, except for 3 nonconservative differences out of the first 11 residues. Nisin has isoleucine at position 1, whereas subtilin has a bulky aromatic tryptophan. Subtilin has a positively-charged lysine at position 2, whereas nisin has an unusual Dhb residue. Finally, subtilin has a negatively-charged glutamate at position 4, whereas nisin has a neutral aliphatic isoleucine.

In previous work, the $Glu_4$ of subtilin was changed to the $Ile_4$ of nisin, and a mutant with enhanced chemical stability and activity was obtained (ref. 21 and U.S. application Ser. No. 07/981,525). The present invention evolved from changing the other two residues at positions 1 and 2 to give a subtilin analog with a nisin-like N-terminus. This analog would have only hydrophobic residues at the N-terminus, as well as a fourth dehydro residue at a location that is unfamiliar to the subtilin processing machinery of *B. subtilis*. If the subtilin-producing organism is unable to process such a mutant protein/gene properly, the entire processing pathway could abort. Since the subtilin machinery of *B. subtilis* cannot process the $S_L$-$Nis_{1-34}$ prepeptide to an active product (22), it is difficult to predict how the subtilin processing machinery would handle the $S_L$-$Nis_{1-11}$-$Sub_{12-32}$ prepeptide.

Construction and expression of the $Nis_{1-11}$-$Sub_{12-32}$ chimera. Using the mutagenesis strategy shown in FIG. 2, residues 1, 2, and 4 in the subtilin structural region were changed to those of nisin. A mutagenesis was performed in the plasmid pSMcat, a cassette-mutagenesis plasmid that contains a copy of the subtilin structural gene upstream from a cat gene (U.S. application Ser. No. 07/981,525 and ref. 21). When this plasmid is transformed into the *B. subtilis* 168 host LHermΔS and selected on chloramphenicol, the subtilin gene is integrated into the chromosomal subtilin (spa) operon (U.S. application Ser. No. 07/981,525 and ref. 21) at the site from which the natural subtilin gene has been deleted. The sequence of the $Nis_{1-11}$-$Sub_{12-32}$ chimera (SEQ ID NO:5) and the nucleotide sequence (SEQ ID NO:4) that encodes it is shown (top), in which the 32-residue mature $Nis_{1-11}$-$Sub_{2-32}$ sequence is numbered. Immediately below are the mutagenic oligonucleotides (SEQ ID NO:6) and (SEQ ID NO:7) used to construct this sequence. The sequence (SEQ ID NO:8) of the $Sub_{1-11}$-$Nis_{12-34}$ chimera (SEQ ID NO:9) and the oligonucleotides (SEQ ID NO:10, SEQ ID NO:11 and SEQ ID NO:12) used to produce it are shown at the bottom.

Figure 3:
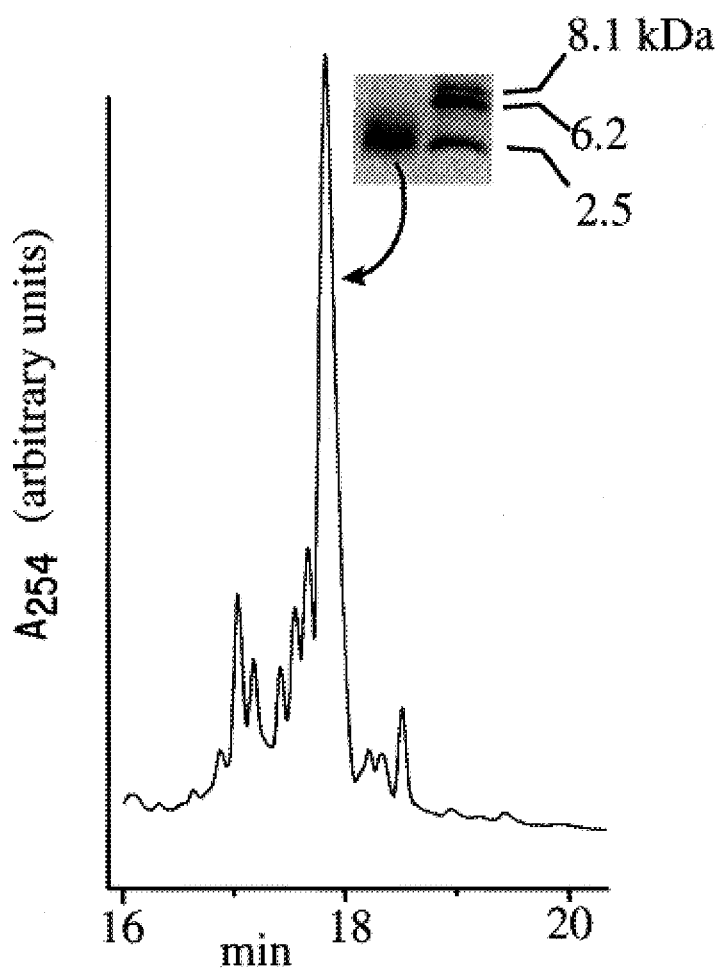
FIG. 3 is an HPLC chromatogram of the $Nis_{1-11}$-$Sub_{12-32}$ chimera constructed as shown in FIG. 2.

The $Nis_{1-11}$-$Sub_{12-32}$ chimeric gene was integrated into the chromosome of *B. subtilis* LHermΔS as described above and cultured as described above. The expressed polypeptide products were isolated from the extracellular fluid and subjected to HPLC chromatography. Samples were collected at 1-min intervals and assayed for activity using the halo assay described herein. FIG. 3 shows the HPLC elution profile of the peptides isolated from cells in early stationary phase. A single large peak emerged from the column, and it possessed antimicrobial activity. Electrophoresis on TRICINE (polyacrylamide)-SDS gels and silver-staining showed a single major band with a relative molecular mass between 3,000 and 3,200, consistent with the predicted molecular weight of the $Nis_{1-11}$-$Sub_{12-32}$ chimera.

The major peak contained the only activity. In FIG. 3, the stained gel is shown in a panel beside the peak (sample, left lane; size standard, right lane). Standards shown in the stained gel are 2.5 kD myoglobin fragment (F3); 6.2 kD myoglobin fragment (F2); and the 8.1 kD myoglobin fragment (F1). The expected mass of the $Nis_{1-11}$-$Sub_{12-32}$ chimera is 3186 Da, which is consistent with the position of the band in the sample lane.

Appearance of a succinylated form of the $Nis_{1-11}$-$Sub_{12-32}$ chimera during late growth stages, as determined by proton NMR and mass spectral analysis. In an attempt to attain a higher yield of material, the culture was allowed to incubate into late stationary phase, whereupon the HPLC column profile showed two peaks, one being the original peak, with a second peak trailing slightly behind (inset, FIG. 4). Hereafter, the first peak is called the "Early Peak," and the second peak is called the "Late Peak." The two peaks ("Early Peak and "Late Peak") were collected separately and subjected to NMR spectroscopy as shown in FIG. 5. The spectra show that the Late Peak is contaminated by the Early Peak. Using the 0–100% acetonitrile gradient described above, these peaks were separated by only 1 min. Consequently, the two expressed forms of the chimera were chromatographed using a shallower gradient (35–60% acetonitrile over 45 min; center, FIG. 4), whereupon the Early Peak and Late Peak were separated by 4 min. Further experiments were performed using the more purified material.

The results of halo assays are shown above the center HPLC profile, with arrows indicating the positions in the profile from which the samples used for halo assays had been derived. The antimicrobial activity is associated mainly with the Early Peak. The halo assays in FIG. 4 do not detect any activity in the Late Peak, but when higher concentrations were tested, its activity was found to be about 10-fold lower than the Early Peak (data not shown). This is reminiscent of the observation that B. subtilis 6633 (the natural producer of subtilin) and LH45 (a subtilin-producing derivative of B. subtilis 168) produce two forms of subtilin (28). When B. subtilis 6633 is incubated into late stationary phase, there is an accumulation of subtilin that has been succinylated at its N-terminus (29). The succinylated subtilin is significantly less active than the normal unsuccinylated subtilin.

The Late Peak was therefore suspected to be the succinylated form of the Early Peak. This was confirmed by mass spectral analysis (FIG. 5), showing that the Early Peak consists mainly of a species with an Mr=3185.98 (panel A), which conforms exactly to the calculated mass of 3185.98 Da expected for the mature $Nis_{1-11}$-$Sub_{12-32}$ chimera. The Late Peak gave a mass of 3286.78 Da (panel B), which is consistent with a calculated mass of 3286.78 Da, corresponding exactly to the 100 Da increase expected from addition of a succinyl group to the mature $Nis_{1-11}$-$Sub_{12-32}$ chimera.

In order for these expected masses to occur, it is necessary for the chimeric prepeptides to have undergone the full panoply of post-translational modifications in which 8 serines and threonines are dehydrated, 5 thioether crosslinkages are formed, and the leader region is cleaved at the proper residue. The NMR spectrum of a mixture of the Early Peak and Late Peak is shown in panel C. Resonances shifted by the presence of the succinyl group are identified by asterisks ($Dhb_2^*$, $Dha_5^*$).

The NMR spectra of the Early Peak (panel D) and of the mixture (panel C) of the Early and Late Peaks show resonances that correspond to the $Dhb_2$ and $Dha_5$ resonances contributed by the nisin part of the molecule and to the $Dhb_{18}$ and $Dha_{31}$ residues contributed by the subtilin portion of the molecule. Identification of the $Dhb_2$, $Dha_5$, $Dhb_{18}$, and $Dha_{31}$ peaks was by correlation with NMR spectra obtained previously for nisin (33) and subtilin (U.S. application Ser. No. 07/981,525 and ref. 21).

Succinylation of subtilin has been shown to cause a shift in the resonance of the $Dha_5$ residue (29), attributable to a change in the chemical environment of $Dha_5$ caused by the presence of the N-terminal succinyl group. Since the $Dhb_2$ residue in the succinylated chimera is even closer to the succinyl group, a shift in its resonance would be expected. The spectrum shown in panel C, which includes resonances of the succinylated chimera, confirms these expectations, and shows a shifted resonance for $Dha_5$ (labeled as $Dha_5^*$), and for $Dhb_2$ (labeled as $Dhb_2^*$). Succinylation of the $Nis_{1-11}$-$Sub_{12-32}$ chimera in the same manner as subtilin also means that the cell treats the chimera in a completely normal way, and that the succinylation system must be able to tolerate the differences in the N-terminal end of the chimera. Consequently, it appears that at least the 5 N-terminal residues of the mature, processed peptide are not critical for recognition by the processing machinery.

The biological activity of the $Nis_{1-11}$-$Sub_{12-32}$ chimera. Nisin and subtilin can inhibit spore-forming food-spoilage bacteria from undergoing outgrowth from spores to the vegetative state, as well as inhibit cells that are in the vegetative state (30). The mechanism of inhibition of these types of cells is different, as it has been shown that the $Dha_5$ residue is critical for subtilin to inhibit spore outgrowth, but not for subtilin to inhibit vegetative cells (31).

The activity of the two purified forms of $Nis_{1-11}$-$Sub_{12-32}$ were therefore measured against outgrowing spores and vegetative cells, and compared to nisin. Since the activities of subtilin and E4I-subtilin have previously been compared to nisin (21), the relative activities among all these forms can be inferred in terms of relative nisin units. The activity of $Nis_{1-11}Sub_{12-32}$ against spore outgrowth was estimated by the halo assay and the liquid assays, and against vegetative cells by the liquid assay.

The $Nis_{1-11}$-$Sub_{12-21}$ chimera was active against both spore outgrowth and vegetative growth. The specific activities of the chimera and nisin were so similar that they could not be distinguished in either their ability to inhibit spore outgrowth or to inhibit vegetative cells (data not shown). Accordingly, one sees inhibition of spore outgrowth at about 0.2 µg/ml, and against vegetative cells at about 2 µg/ml, with both the chimera and nisin. Based on previous measurements (21, 26, 31), this means that the $Nis_{1-11}$-$Sub_{12-32}$ chimera is about 2-fold more active than E4I-subtilin, and about 6–8 times more active than natural subtilin.

Stability of the dehydro residues in the $Nis_{1-11}$-$Sub_{12-32}$ chimera during incubation in aqueous solution. The chemical and biological instability of subtilin have been correlated with the tendency of residue $Dha_5$ to spontaneously undergo chemical modification which results in disappearance of the $Dha_5$ peak in the NMR spectrum, and loss of activity against spores (21, 28, 32). This instability of residue $Dha_5$ has been attributed to the participation of the carboxyl group of the $Glu_4$ residue of subtilin in the modification process. Accordingly, changing $Glu_4$ to $Ile_4$ (E4I-subtilin) dramatically enhances the chemical stability of the $Dha_5$ residue (U.S. application Ser. No. 07/981,525 and ref. 21), with the chemical half-life of the $Dha_5$ residue increasing nearly 60-fold, from less than a day to 48 days. Since the $Nis_{1-11}$-$Sub_{12-32}$ chimera has additional changes in the vicinity of the $Dha_5$ residue, the chemical stability of the dehydro residues was examined by taking the NMR spectrum of a sample that was incubated in aqueous solution for an extended period of time.

Figure 4:
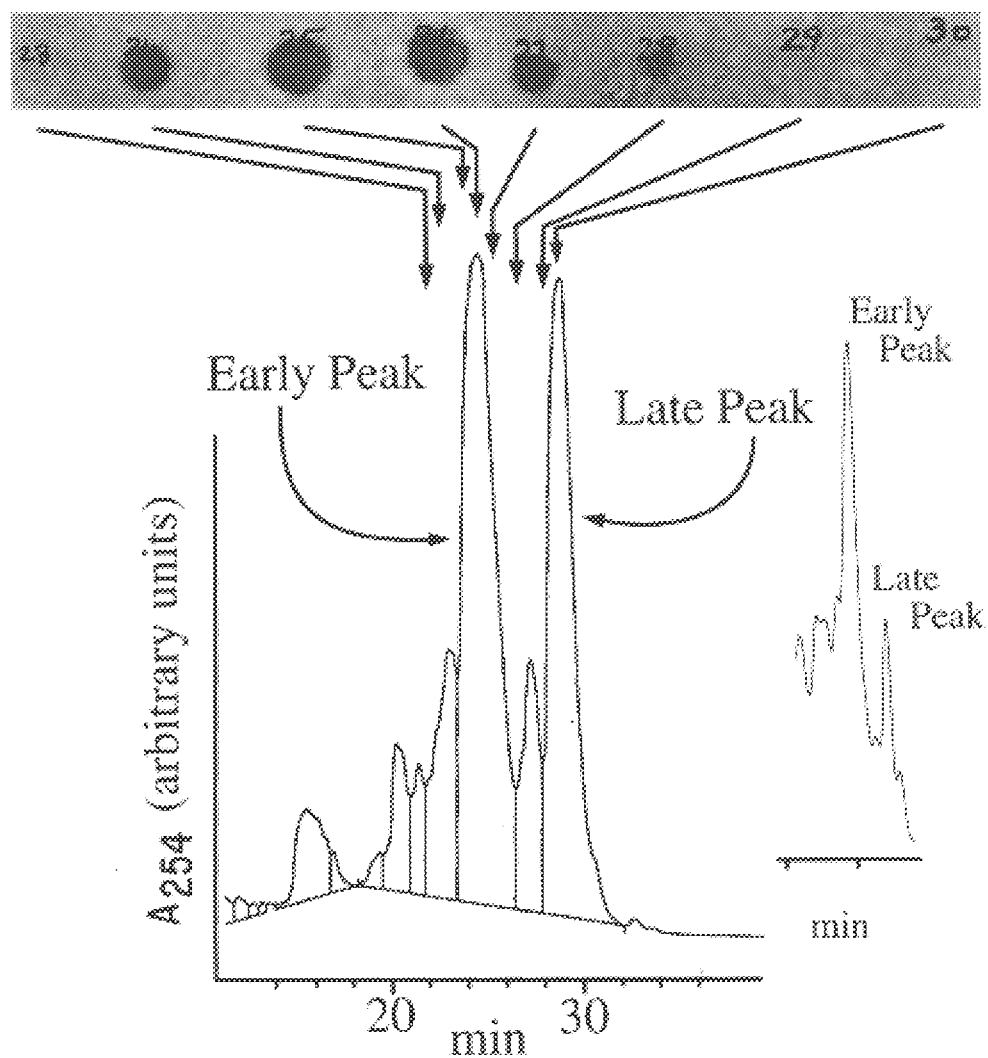
FIG. 4 shows the resolution of the $Nis_{1-11}$-$Sub_{12-32}$ chimera into two forms on the HPLC column (inset), resulting in the appearance of a new peak; the $Nis_{1-11}$-$Sub_{12-32}$ chimera was constructed as shown in FIG. 2 and expressed and isolated as described below except that the cells were grown for a longer time (into the stationary phase)
Figure 5:
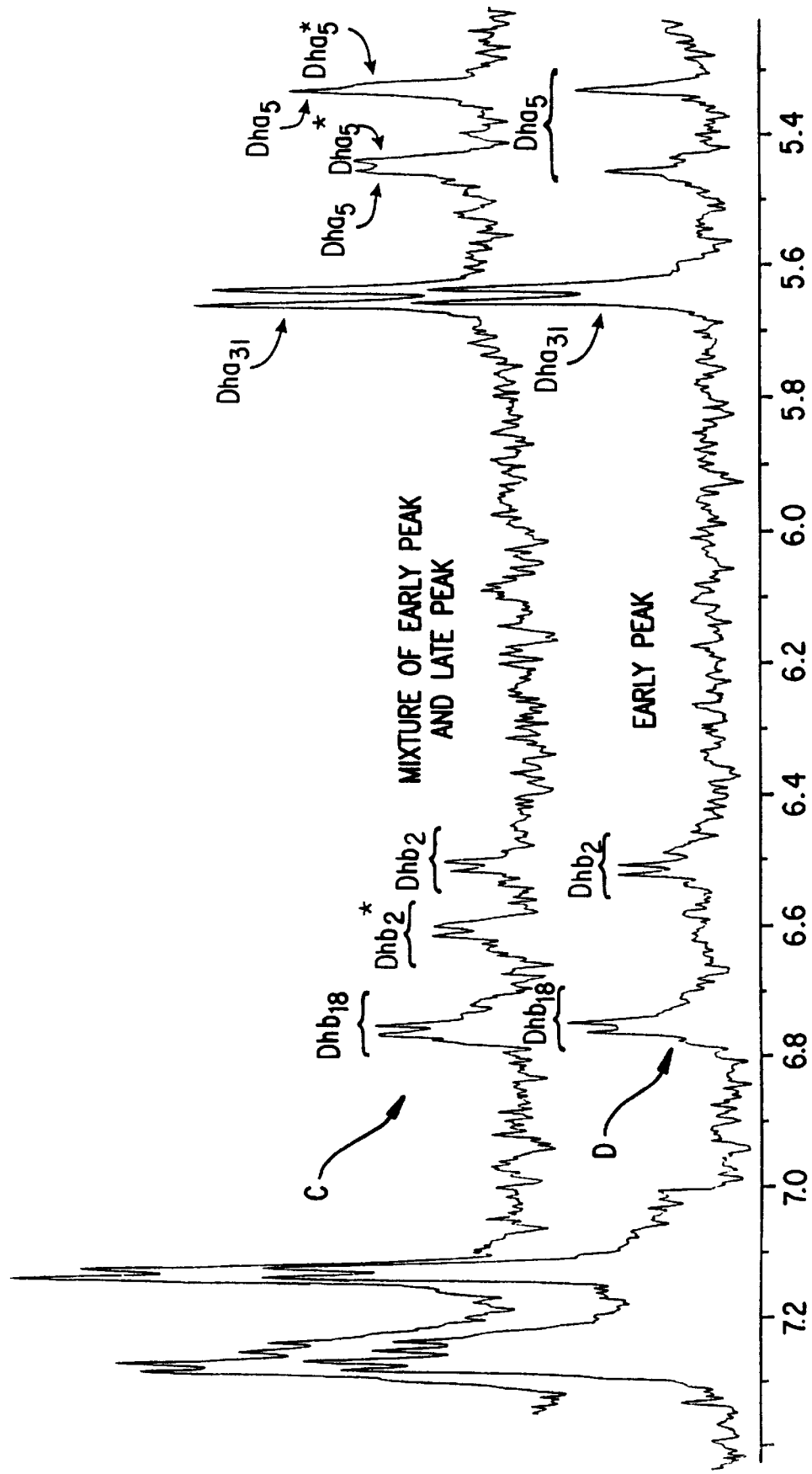
FIG. 5 shows the NMR and mass spectra of the Early Peak and Late Peak, as defined in the HPLC elution profiles in FIG. 4.
Figure 5B:
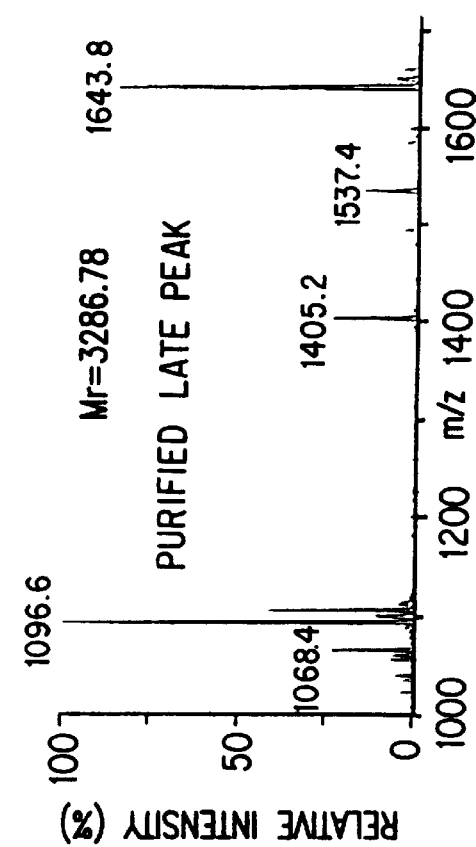
Figure 5A:
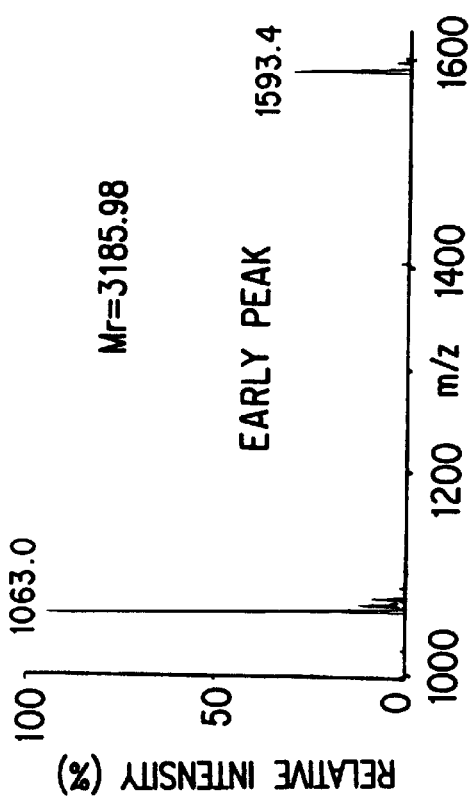
Figure 6:
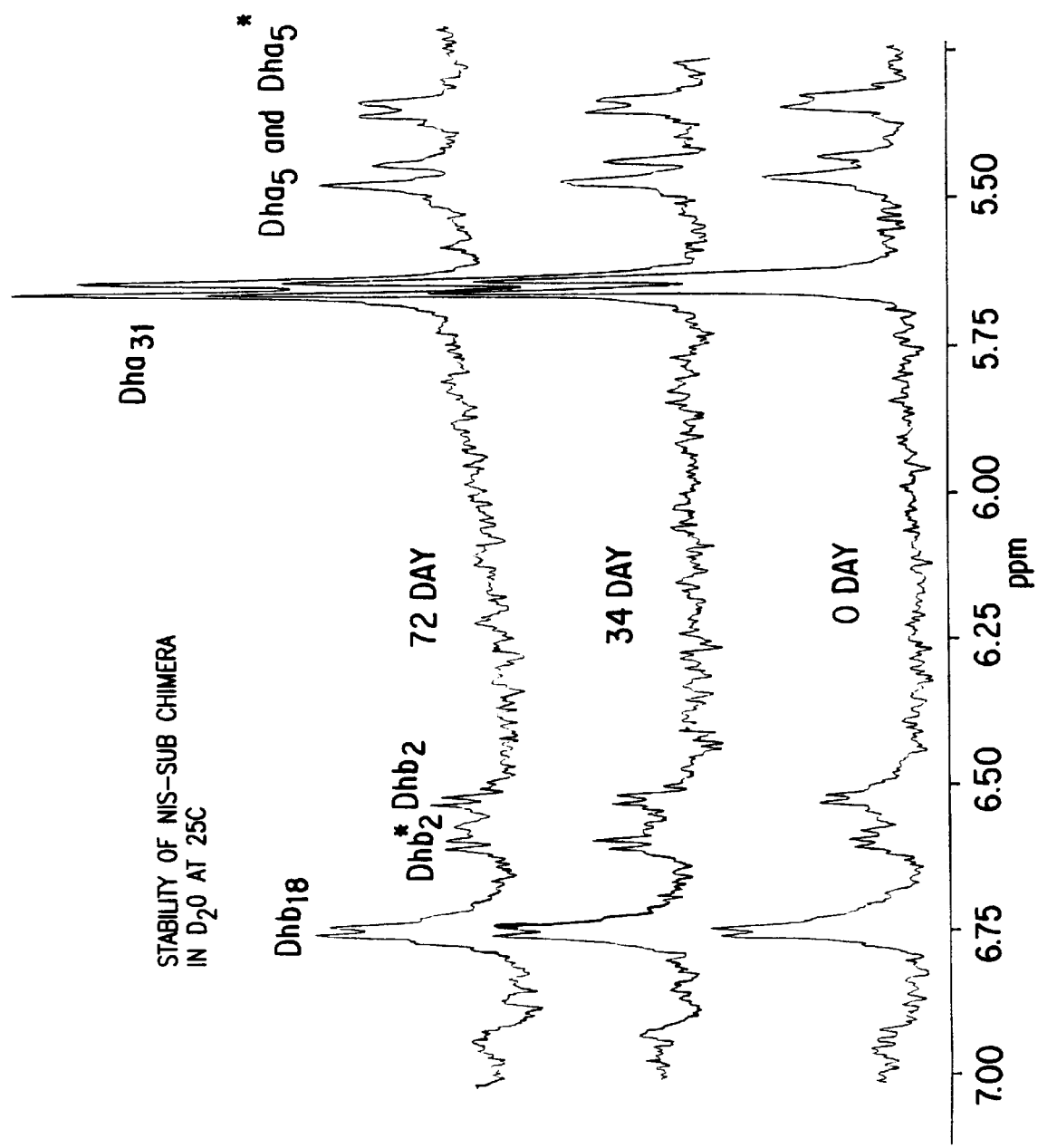
FIG. 6 shows the NMR spectra of the $Nis_{1-11}$-$Sub_{12-32}$ chimera during the course of a 72-day incubation, demonstrating the stability of the chimera.

A 3 mg amount of the $Nis_{1-11}$-$Sub_{12-32}$ chimera (consisting of a mixture of the Early Peak and Late Peak as defined in FIGS. 4 and 5) was dissolved in $D_2O$ at a pH of 6.0, placed in an NMR tube (which was then closed), and incubated in aqueous solution in the dark at room temperature for 2.5 months. The NMR spectrum of this sample was determined after 0, 34, and 72 days, with the results shown in FIG. 6. The NMR spectrum of the $Nis_{1-11}$-$Sub_{12-32}$ chimera shows the expected resonances of $Dhb_2$, $Dhb_2^*$, $Dha_5$, $Dha_5^*$, $Dhb_8$, and $Dha_{31}$. There was no significant change in the resonances of the dehydro residues during the course of the 72-day incubation period.

The slight differences that are seen are readily attributable to variations introduced during baseline correction during computations with the spectral data. In contrast to the 0.8-day half-life of the $Dha_5$ residue in natural subtilin and its 48-day half-life in E4I-subtilin, the half-life of the $Dha_5$ residue in the $Nis_{1-11}Sub_{12-32}$ chimera is so long that it cannot be estimated from the 72-day time-point. Longer incubation times were not performed. Therefore, the dehydro residues in the $Nis_{11-11}$-$Sub_{12-32}$ chimera are extremely stable.

These results demonstrate that the $Dha_5$ residue is subject to profound changes in its chemical reactivity, ranging from the most reactive state observed in natural subtilin to the least reactive state observed in the $Nis_{1-11}$-$Sub_{12-32}$ chimera, E4I-subtilin having an intermediate state of reactivity. Somewhat surprisingly, the biological activity displayed by these structural variants varies inversely with the reactivity, with the unstable and highly reactive subtilin having the lowest biological activity, and the highly stable $Nis_{1-11}$-$Sub_{12-32}$ chimera displaying the greatest biological activity. The fact that the chemical reactivity of $Dha_5$ varies inversely with biological activity argues that role of the $Dha_5$ residue in the antimicrobial mechanism is not related to its chemical reactivity in a simple fashion, and that other factors, such as the specificity imposed by the peptide sequence surrounding the dehydro residue, may also be important.

Properties of the $Sub_{1-11}$-$Nis_{12-34}$ "Reverse Chimera". An important feature of the $S_L$-$Nis_{1-11}$-$Sub_{12-32}$ chimeric prepeptide is that the subtilin processing machinery is able to correctly recognize and process it into its corresponding mature form. Since the same machinery in *B. subtilis* does not successfully process S-$Nis_{1-34}$, there could be something in the $Nis_{12-34}$ region that disturbs the subtilin processing machinery of *B. subtilis*. If this is the case, the subtilin processing machinery should not be able to correctly process a chimera that contains the $Nis_{12-34}$ region.

Accordingly, a reverse chimera was constructed ($S_L$-$Sub_{1-11}$-$Nis_{12-34}$), containing a subtilin sequence at the N-terminus of the structural region and nisin sequence at the C-terminus. This chimera was constructed using the strategy described in FIG. 2. The synthetic gene containing the "reverse" chimera was integrated into the chromosome of LHermΔS and expressed. The corresponding polypeptide was recovered from the culture supernatant using the butanol-acetone extraction method, and further purified by RP-HPLC as shown in FIG. 7.

Figure 7:
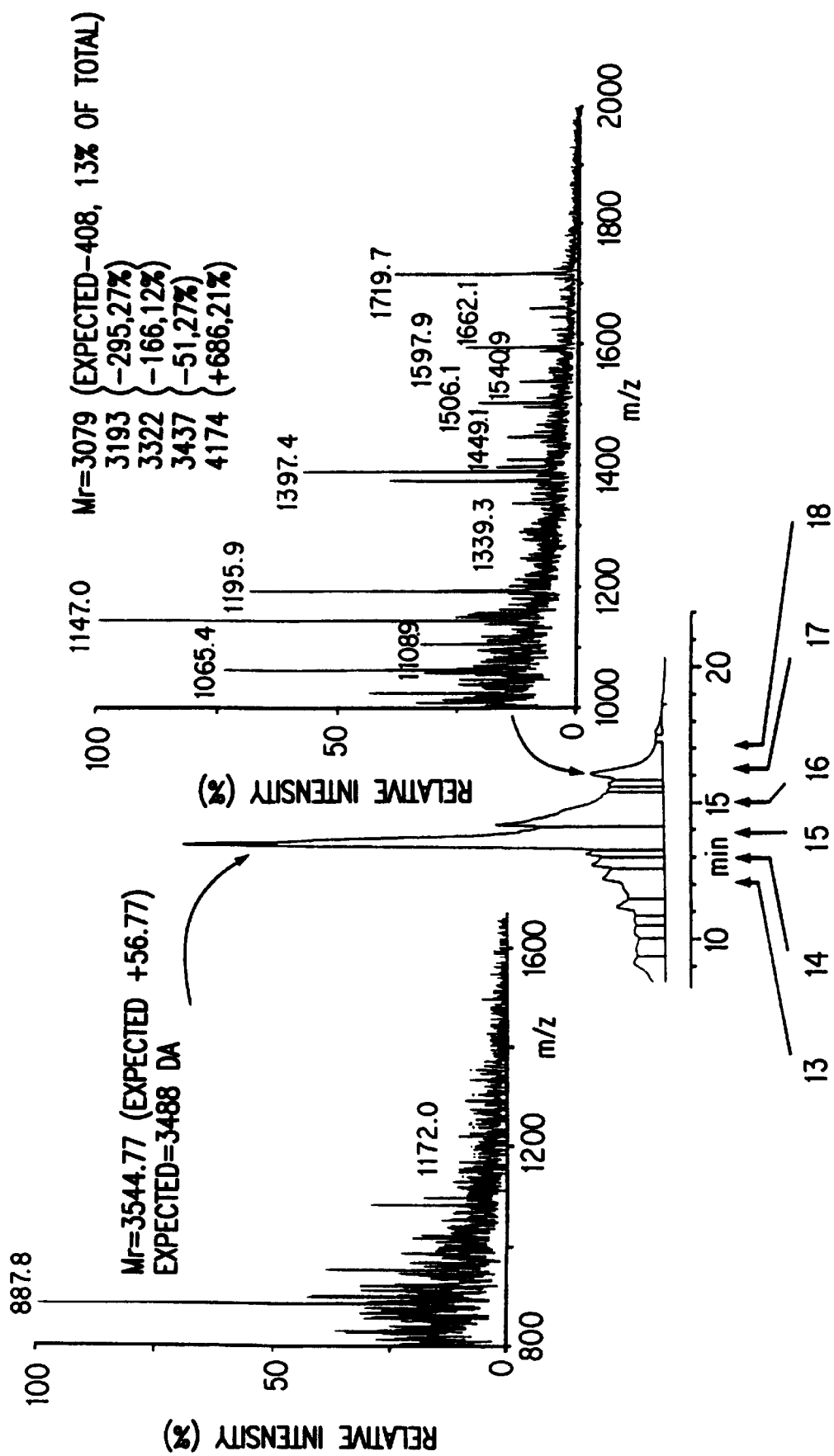
FIG. 7 shows HPLC profiles and mass spectra of the $Sub_{1-11}$-$Nis_{12-34}$ chimera.

The HPLC profile of the $Sub_{11-11}$-$Nis_{12-34}$ chimera is shown in the center of FIG. 7. A major peak emerged somewhat earlier than expected for the $Sub_{1-11}$-$Nis_{12-34}$ chimera, but it was devoid of activity. Moreover, mass spectral analysis of the protein corresponding this major peak showed an Mr=3544.47 Da, which is about 56 mass units, or 3 water molecules, greater than the expected 3488 Da. Thus, it could be that three dehydration reactions failed to occur in the processing of the prepeptide.

Following this large peak was a small peak (also shown in FIG. 7) that showed activity in the halo assay. The amount of material in this peak is quite small. Mass spectral analysis shows the material of the small peak to be very heterogeneous, consisting of at least a half-dozen species, none of which have the molecular mass expected for the $Sub_{1-11}$-$Nis_{12-34}$ chimera. Instead of an expected mass of 3488 Da, values of 3079 (expected Mr−408; 13% of the total amount of peptides identified and analyzed in the minor peak), 3193 (Mr−295; 27%), 3322 (Mr−166; 12%), 3437 (Mr−51; 27%), and 4174 (Mr+686; 21%) were obtained. None of these masses are readily explained in terms of simple processing defects, such as the absence of dehydrations to give $Dha_5$ and $Dha_{33}$ (there is no Dhb expected), or the leader peptide not being cleaved. The small size of several species indicates that proteolysis may have occurred.

The halo assays of samples from the profile are shown at the bottom of FIG. 7, with the arrows showing the samples which were derived from the profile. The only activity in the profile corresponded to the position of the small peak appearing at 16 min. The mass spectrum at the left was obtained for the material in the large peak indicated by the arrow. The mass spectrum at the right was obtained for the material in the small peak (which was active) indicated by the other arrow.

The active specie(s) from production of the $Sub_{1-11}$-$Nis_{12-34}$ chimera in a subtilin-producing microorganism have not yet been conclusively determined. However, the specific activity of whatever specie(s) are responsible for the inhibitory activity is much higher than nisin itself.

For example, the total area of the active peak consists of no more than 10 µg of peptide, of which 0.13 µg was used for the halo assay shown in FIG. 7. This small quantity of peptide possesses an activity equivalent to 0.5 µg of nisin (data not shown). If all of the components in the minor peak were equally active, they would be about 4-fold (0.5 µg÷0.13) more active than nisin. The amount of the various components in the minor peak ranges from about 12% to about 27% of the total. If all of the activity is due to just one of the components, then the active component would be about 15 to 35 times as active as nisin, depending on the percentage of active component in the minor peak.

Determining the active species and the activities thereof will require that the active component be purified to homogeneity and studied further. This can be accomplished by the procedures described herein (for example, by HPLC using a shallower gradient, as described above for separation of succinylated $Nis_{1-11}$-$Sub_{12-32}$, and by determining biological activity as described above). Although we do not conclusively know which factors contribute to this high activity, the discovery of this high activity is completely unexpected, and will lead to the design of lantibiotic analogs with superior antimicrobial properties.

DISCUSSION

The ability to incorporate the unusual dehydro and lanthio-type amino acids into lantibiotic analogs and non-lantibiotic polypeptides depends on the ability of the lantibiotic processing machinery to cope with foreign precursor sequences. Our working hypothesis is that the leader region is primarily responsible for engaging the prepeptide with the processing machinery, and once engaged, serines and threonines are dehydrated with little regard for the sequence in which they reside. Cysteines then react with particular dehydro residues in accordance with the forces of folding and conformation that exist within the polypeptide in a manner that is reminiscent of the specific selection of disulfide-bond partners in polypeptides such as ribonuclease A and insulin (33). There are now several known instances in which pre-lantibiotic peptides undergo processing reactions, but give rise to inactive products. These instances are summarized in Table 1. Examples include the $S_L$-$Nis_{1-34}$ chimera that produces a processed (22) but inactive (22, 23) product when expressed in a cell that possesses the subtilin machinery, and the present $S_L$-$Sub_{1-11}$-$Nis_{12-34}$ chimera that produces a heterogeneous mixture of products that are mainly inactive, although at least one active form is produced.

Although $N_L$-$Nis_{1-34}$ is an authentic lantibiotic precursor, the subtilin processing machinery seems incapable of processing it, and its gene products have not been detected in *B. subtilis* (22, 23). However, if the subtilin leader is placed in front of the nisin structural region to give $S_L$-$Nis_{1-34}$, a processed, but inactive, product is produced by the subtilin machinery of *B. subtilis* (22). Thus, the subtilin leader is competent in engaging the *B. subtilis* processing machinery, but there is something about the conformational and folding interactions between the leader and structural region in the $S_L$-$Nis_{1-34}$ construct that causes some of the processing reactions (perhaps the "partner" selection in thioether formation) to malfunction. The fact that the $S_{L(1-7)}$-$N_{L(8-23)}$-$Nis_{1-34}$ construct is processed properly to give active nisin (23) argues that critical conformational interactions are restored when an appropriate N-terminal sequence element from the subtilin leader region is combined with a C-terminal sequence element of the nisin leader.

between the N-terminal portion of the leader region and the C-terminal portion of the structural region of certain constructs. The results herein also provide new insight about the relationship between the structure of lantibiotics and their chemical properties and biological activity. Subtilin and nisin are highly disparate in their chemical stability and specific activity, with nisin being superior to subtilin in both categories. The $Nis_{1-11}$-$Sub_{12-32}$ chimera has the superior properties of nisin, showing that the three residues that differ in the N-terminal regions of nisin and subtilin are primarily responsible for the disparity between nisin and subtilin.

$Nis_{1-11}$-$Sub_{12-32}$ has a very hydrophobic N-terminal region, which may facilitate insertion of the lantibiotic into the membrane, which is its target of action (26, 34–36). However, another possible explanation for the elevated activity of nisin the presence of a second dehydro residue

TABLE 1

| Prepeptide Sequence | Strain in which expressed | Prepeptide is processed | Peptide is secreted into extracellular medium | Secreted peptide is active | Ref. |
|---|---|---|---|---|---|
| $S_L$-$S_{1-32}$ | *B. subtilis* 6633 | yes | yes | yes | a |
|  | *B. subtilis* 168 | yes | yes | yes | b |
| $N_L$-$Nis_{1-34}$ | *L. lactis* 11454 | yes | yes | yes | c |
|  | *B. subtilis* 6633 | no | no | na | d |
|  | *B. subtilis* 168 | no | no | na | e |
| $S_L Nis_{1-34}$ | *L. lactis* | yes | yes | no | f |
| $S_L Nis_{1-34}$ | *B. subtilis* 6633 | yes | yes | no | g |
| $S_{L(1-7)}$-$N_{L(8-23)}$-$Nis_{1-34}$ | *B. subtilis* 6633 | yes | yes | yes | h |
| $S_L$-$Nis_{1-11}$-$Sub_{12-32}$ | *B. subtilis* 168 | yes | yes | yes | This work |
| $S_L$-$Sub_{1-11}$-$Nis_{12-34}$ | *B. subtilis* 168 | heterogeneous | yes | partially | This work |

Refs: a. (18), b. (21), c. (17), d. (22, 23), e. unpublished, f. (24) g. (22, 23), h. (23). "na" means not applicable.

However, this combination of leader sequence elements must be appropriately complemented by the structural region. Whereas the $S_L$-$Nis_{1-11}$-$Sub_{12-32}$ construct is processed correctly, the $S_L$-$Sub_{1-11}$-$Nis_{12-34}$ construct is not. However, it is expected that determination of three non-dehydrated serine and/or threonine residues in the major product, subject to one or more appropriate enzyme(s) of the subtilin processing machinery (e.g., contacted with an appropriate subtilin-producing microorganism) may lead to production of a biologically active lantibiotic. Moreover, the processing reactions for the latter construct when expressed in *B. subtilis* give a complex mixture of mainly inactive products.

Surprisingly, at least one component in this mixture of product is active. None of the components of the $S_L$-$Sub_{1-11}$-$Nis_{12-34}$ product mixture had the mass of a correctly-processed product, however. Therefore, the activity of the minor product(s) must be due to an incorrectly-processed component. Quite surprisingly, the specific activity of the active component of the minor product(s) was at least 4-fold and as much as 35-fold higher than nisin itself. The knowledge about what is responsible for such high activity may provide insight about the design of lantibiotics which are dramatically more effective than the natural forms.

In conclusion, correct processing of the pre-lantibiotic peptide may require specific conformational communication (Dhb) at position 2 in the $Nis_{1-11}$-$Sub_{12-32}$ chimera. One might expect that the $Dhb_2$ would have a dramatic effect on the antimicrobial properties of the chimera, since it is so close to the critical $Dha_5$ and might cooperate in reacting with its microbial target. However, even if $Dhb_2$ does affect the antimicrobial properties, there may be no more than a 2-fold effect.

This illustrates a frustrating aspect of our knowledge about lantibiotics. The ubiquitous occurrence of the unusual residues among the many known lantibiotics argues that they are conserved because they have important functions. However, except for the critical role of $Dha_5$ in inhibition of spore outgrowth, functions that clearly justify this ubiquitous occurrence have yet to be fully elucidated.

Obviously, numerous modifications and variations of the present invention are possible in light of the above teachings. It is therefore to be understood that within the scope of the appended claims, the invention may be practiced otherwise than as specifically described herein.

REFERENCES

1. Hansen, J. N. (1993) in *Annual Review of Microbiology*, Vol. 47 (Ornston, L. N., ed.), pp. 535–564, Annual Reviews, Inc., Palo Alto, Calif.
2. Hansen, J. N. (1994) in *CRC Critical Reviews in Food Science and Nutrition*, Vol. 34 (Clydesdale, F. M., ed.), pp. 69–93, CRC Press, Inc., Boca Raton, Fla.

3. Sahl, H.-G. (1994) in *Antimicrobial Peptides*. Ciba Foundation Symposium (Marsh, J., and Goode, J. A., eds.), pp. 27–53, John Wiley & Sons, Ltd., Chichester, England.
4. Marsh, J., and Goode, J. A., eds. (1994) *Antimicrobial Peptides*. Ciba Foundation Symposium, John Wiley & Sons, Ltd., Chichester, England.
5. Bevins, C. (1994) in *Antimicrobial Peptides*. Ciba Foundation Symposium 186 (Marsh, J., and Goode, J. A., eds.), pp. 250–269, John Wiley & Sons, Ltd., Chichester, England.
6. Boman, H. G. (1991) *Cell* 65, 205–207.
7. Zasloff, M. Martin, B., and Chen, H. C. (1988) *Proc. Natl. Acad. Sci. U.S.A*. 85, 910–913.
8. Zasloff, M. (1987) *Proc. Natl. Acad. Sci. U.S.A*. 84, 5449–5453.
9. Cuervo, J. H., Rodriguez, B., and Houghten, R. A. (1988) *Pept. Res*. 1, 81–86.
10. Lehrer, R. I., Ganz, T., and Selsted, M. E. (1991) *Cell* 64, 229–230.
11. Selsted, M. E., Harwig, S. S., Ganz, T., Schilling, J. W., and Lehrer, R. I. (1985) *J. Clin. Invest*. 76, 1436–1439.
12. Hill, C. P., Yee, J., Selsted, M. E., and Eisenberg, D. (1991) *Science* 251, 1481–1485.
13. Lepage, P., Bitsch, F., Roecklin, D., Keppi, E., Dimarcq, J. L., Reichhart, J. M., Hoffmann, J. A., Roitsch, C., and Van Dorseelaer, A. (1991) *Eur. J. Biochem*. 196, 735–742.
14. Morishima, I., Suginaka, S., Ueno, T., and Hirano, H. (1990) *Comp. Biochem. Physiol. [B]*. 95, 551–554.
15. Boman, H. G., Faye, I., von Hofsten, P., Kockum, K., Lee, J. Y., Xanthopoulos, K. G., Bennich, H., Engstrom, A., Merrifield, R. B., and Andreu, D. (1985) *Dev. Comp. Immunol*. 9, 551–558.
16. Hurst, A. (1981) in *Adv. Appl. Microbiol*., Vol. 27 (Perlman, D., and Laskin, A. I., eds.), pp. 85–123, Academic Press, New York.
17. Buchman, G. W., Banerjee, S., and Hansen, J. N. (1988) *J. Biol. Chem*. 263, 16260–16266.
18. Banerjee, S., and Hansen, J. N. (1988) *J. Biol. Chem*. 263, 9508–9514.
19. van der Meer, J. R., Rollema, H. S., Siezen, R. J., Beerthuyzen, M. M., Kuipers, O. P., and de Vos, W. M. (1994) *J. Biol. Chem*. 269, 3555–3562.
20. Kuipers, O. P., Rollema, H. S., Yap, W. M., Boot, H. J., Siezen, R. J., and de Vos, W. M. (1992) *J. Biol. Chem*. 267, 24340–24346.
21. Liu, W., and Hansen, J. N. (1992) *J. Biol. Chem*. 267, 25078–25085.
22. Hawkins, G. (1990) *Ph.D. Thesis: Investigation of the site and mode of action of the small protein antibiotic subtilin and development and characterization of an expression system for the small protein antibiotic nisin in Bacillus subtilis*, University of Maryland, College Park, Md.
23. Rintala, H., Graeffe, T., Paulin, L., Kalkkinen, N., and Saris, P. E. J. (1993) *Biotech. Lett*. 15, 991–996.
24. Kuipers, O. P., Rollema, H. S., de Vos, W. M., and Siezen, R. J. (1993) *FEBS Lett*. 330, 23–27.
25. Feeney, R. E., Garibaldi, J. A., and Humphreys, E. M. (1948) *Archiv. Biochem. Biophys*. 17, 435–445.
26. Morris, S. L., Walsh, R. C., and Hansen, J. N. (1984) *J. Biol. Chem*. 21, 13590–13594.
27. Schagger, H., and von Jagow, G. (1987) *Anal. Biochem*. 166, 368–379.
28. Hansen, J. N., Chung, Y. J., Liu, W., and Steen, M. J. (1991) in *Nisin and Novel Lantibiotics* (Jung, G., and Sahl, H.-G., eds.), pp. 287–302, ESCOM, Leiden, The Netherlands.
29. Chan, W. C., Bycroft, B. W., Leyland, M. L., Lian, L. Y., and Roberts, G. C. (1993) *Biochem. J*. 291, 23–27.
30. Hurst, A. (1981) *Adv. Appl. Microbiol*. 27, 85–123.
31. Liu, W., and Hansen, J. N. (1993) *Appl. Environ. Microbiol*. 59, 648–651.
32. Liu, W., and Hansen, J. N. (1990) *Appl. Environ. Microbiol*. 56, 2551–2558.
33. Anfinsen, C. B. (1973) *Science* 181, 223–230.
34. Kordel, M., Schuller, F., and Sahl, H.-G. (1989) *FEBS Lett*. 244, 99–102.
35. Schuller, F., Benz, R., and Sahl, H.-G. (1989) *Eur. J. Biochem*. 182, 181–186.
36. Benz, R., Jung, G., and Sahl, H.-G. (1991) in *Nisin and Novel Lantibiotics* (Jung, G., and Sahl, H.-G., eds.), pp. 359–372, ESCOM, Leiden, The Netherlands.
37. Gross, E. (1975) in Peptides: *Chemistry, Structure, and Biology* (Walter, R., and Meienhofer, J., eds.), pp. 31–42, Ann Arbor Science, Ann Arbor, Mich.
38. Gross, E. (1978) in *Antibiotics. Isolation, Separation and Purification* (Weinstein, M. J., and Wageman, G. H., eds.), pp. 415–462, Elsevier, N.Y.
39. Gross, E., Kiltz, H. H., and Nebelin, E. (1973) *Hoppe-seyler's Z Physiol. Chem*. 354, 810–812.

What is claimed as new and desired to be secured by Letters Patent of the United States is:

1. A mutant or chimeric lantibiotic of the formula:

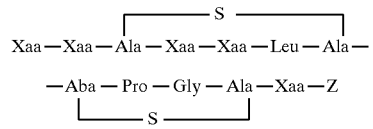

wherein

Z is $Sub_{13\text{-}32}$,

Xaa at the 1-position is Trp, Phe or Tyr; Xaa at the 2-position is Lys, Arg or His; Xaa at the 4-position is Ile, Gly, Ala, Val, or Leu; Xaa at the 5-position is Dha; and Xaa at the 12-position is Val, Ile, Gly, Ala or Leu, and wherein said lantibiotic has antimicrobial activity, with the proviso that, simultaneously, the 1-position, the 2-position, the 4 position and the 5-position are not, respectively, Trp, Lys, Ile, and Dha or Ala.

2. The mutant or chimeric lantibiotic of claim 1, where Xaa at the 1-position is Trp; Xaa at the 2-position is Lys; Xaa at the 4-position is Gly, Ala, Val, or Leu; and Xaa at the 12-position is Val.

3. The mutant or chimeric lantibiotic of claim 1, where Xaa at the 1-position is Trp; Xaa at the 2-position is Lys; Xaa at the 4-position is Ile; Xaa at the 5-position is Dha; and Xaa at the 12-position is Val, subject to said proviso.

4. The mutant or chimeric lantibiotic of claim 1, having the sequence $Nis_{1\text{-}11}\text{-}Sub_{12\text{-}32}$.

5. The mutant or chimeric lantibiotic of claim 1 produced by a process comprising:

culturing, in a suitable culture medium, a lantibiotic-producing host transformed with (1) a polynucleic acid encoding the lantibiotic, (2) an expression vector comprising the polynucleic acid or (3) a plasmid comprising the polynucleic acid; and recovering the mutant or chimeric lantibiotic from the culture medium.

6. The mutant or chimeric lantibiotic of claim 1, having an antimicrobial activity at least equal to that of nisin.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Modified-site
        ( B ) LOCATION: 2..3
        ( D ) OTHER INFORMATION: /product="OTHER"
            / note= "Dehydrobutyrine (Dhb)"

( i x ) FEATURE:
    ( A ) NAME/KEY: Modified-site
    ( B ) LOCATION: 3..7
    ( D ) OTHER INFORMATION: /product="OTHER"
        / note= "Positions 3 and 7 are lanthionine."

( i x ) FEATURE:
    ( A ) NAME/KEY: Modified-site
    ( B ) LOCATION: 5..6
    ( D ) OTHER INFORMATION: /product="OTHER"
        / note= "Dehydroalanine (Dha)"

( i x ) FEATURE:
    ( A ) NAME/KEY: Modified-site
    ( B ) LOCATION: 8..11
    ( D ) OTHER INFORMATION: /product="OTHER"
        / note= "Positions 8 and 11 are beta-methyllanthionine."

( i x ) FEATURE:
    ( A ) NAME/KEY: Modified-site
    ( B ) LOCATION: 13..19
    ( D ) OTHER INFORMATION: /product="OTHER"
        / note= "Positions 13 and 19 are beta-methyllanthionine."

( i x ) FEATURE:
    ( A ) NAME/KEY: Modified-site
    ( B ) LOCATION: 23..26
    ( D ) OTHER INFORMATION: /product="OTHER"
        / note= "Positions 23 and 26 are beta-methyllanthionine."

( i x ) FEATURE:
    ( A ) NAME/KEY: Modified-site
    ( B ) LOCATION: 25..28
    ( D ) OTHER INFORMATION: /product="OTHER"
        / note= "Positions 25 and 28 are beta-methyllanthionine."

( i x ) FEATURE:
    ( A ) NAME/KEY: Modified-site
    ( B ) LOCATION: 33..34
    ( D ) OTHER INFORMATION: /product="OTHER"
        / note= "Dehydroalanine (Dha)"

( x i ) SEQUENCE DESCRIPTION: SEQ ID NO:1:

```
Ile  Xaa  Xaa  Ile  Xaa  Leu  Xaa  Xaa  Pro  Gly  Xaa  Lys  Xaa  Gly  Ala  Leu
 1              5                        10                       15

Met  Gly  Xaa  Asn  Met  Lys  Xaa  Ala  Xaa  Xaa  His  Xaa  Ser  Ile  His  Val
         20                       25                       30

Xaa  Lys
```

( 2 ) INFORMATION FOR SEQ ID NO:2:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Modified-site
        ( B ) LOCATION: 3..7
        ( D ) OTHER INFORMATION: /product="OTHER"
            / note= "Positions 3 and 7 are lanthionine."

( i x ) FEATURE:
        ( A ) NAME/KEY: Modified-site
        ( B ) LOCATION: 5..6
        ( D ) OTHER INFORMATION: /product="OTHER"
            / note= "Dehydroalanine (Dha)"

( i x ) FEATURE:
        ( A ) NAME/KEY: Modified-site
        ( B ) LOCATION: 8..11
        ( D ) OTHER INFORMATION: /product="OTHER"

/ note= "Positions 8 and 11 are beta-methyllanthionine."

( i x ) FEATURE:
    ( A ) NAME/KEY: Modified-site
    ( B ) LOCATION: 13..19
    ( D ) OTHER INFORMATION: /product="OTHER"
        / note= "Positions 13 and 19 are beta-methyllanthionine."

( i x ) FEATURE:
    ( A ) NAME/KEY: Modified-site
    ( B ) LOCATION: 18..19
    ( D ) OTHER INFORMATION: /product="OTHER"
        / note= "Dehydrobutyrine (Dhb)"

( i x ) FEATURE:
    ( A ) NAME/KEY: Modified-site
    ( B ) LOCATION: 23..26
    ( D ) OTHER INFORMATION: /product="OTHER"
        / note= "Positions 23 and 26 are beta-methyllanthionine."

( i x ) FEATURE:
    ( A ) NAME/KEY: Modified-site
    ( B ) LOCATION: 25..28
    ( D ) OTHER INFORMATION: /product="OTHER"
        / note= "Positions 25 and 28 are beta-methyllanthionine."

( i x ) FEATURE:
    ( A ) NAME/KEY: Modified-site
    ( B ) LOCATION: 31..32
    ( D ) OTHER INFORMATION: /product="OTHER"
        / note= "Dehydroalanine (Dha)"

( x i ) SEQUENCE DESCRIPTION: SEQ ID NO:2:

```
Trp Lys Xaa Glu Xaa Leu Xaa Xaa Pro Gly Xaa Val Xaa Gly Ala Leu
1               5                   10                  15

Gln Xaa Xaa Phe Leu Gln Xaa Leu Xaa Xaa Asn Xaa Lys Ile Xaa Lys
            20                  25                  30
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Modified-site
        ( B ) LOCATION: 3..7
        ( D ) OTHER INFORMATION: /product="OTHER"
            / note= "Positions 3 and 7 are lanthionine."

( i x ) FEATURE:
        ( A ) NAME/KEY: Modified-site
        ( B ) LOCATION: 8..11
        ( D ) OTHER INFORMATION: /product="OTHER"
            / note= "Positions 8 and 11 are beta-methyllanthionine."

( i x ) FEATURE:
        ( A ) NAME/KEY: Peptide
        ( B ) LOCATION: 13
        ( D ) OTHER INFORMATION: /note= "Position 13 represents
            either positions 13-34 of Nisin or positions 13-32 of
            subtilin."

( x i ) SEQUENCE DESCRIPTION: SEQ ID NO:3:

```
Xaa Xaa Xaa Xaa Xaa Leu Xaa Xaa Pro Gly Xaa Xaa Xaa
1               5                   10
```

( 2 ) INFORMATION FOR SEQ ID NO:4:

( i ) SEQUENCE CHARACTERISTICS:
        ( A ) LENGTH: 127 base pairs ( B ) TYPE: nucleic acid
( C ) STRANDEDNESS: unknown
( D ) TOPOLOGY: linear ( i i ) MOLECULE TYPE: other nucleic acid
( A ) DESCRIPTION: /desc = "Synthetic DNA"

( i x ) FEATURE:
( A ) NAME/KEY: CDS
( B ) LOCATION: 1..117

( x i ) SEQUENCE DESCRIPTION: SEQ ID NO:4:

```
GAT  TCG  AAA  ATC  ACT  CCG  CAA  ATC  ACT  AGT  ATT  TCA  CTT  TGT  ACA  CCC       48
Asp  Ser  Lys  Ile  Thr  Pro  Gln  Ile  Thr  Ser  Ile  Ser  Leu  Cys  Thr  Pro
 1              5                        10                       15

GGG  TGT  GTA  ACT  GGT  GCA  TTG  CAA  ACT  TGC  TTC  CTT  CAA  ACA  CTA  ACT       96
Gly  Cys  Val  Thr  Gly  Ala  Leu  Gln  Thr  Cys  Phe  Leu  Gln  Thr  Leu  Thr
              20                       25                       30

TGT  AAC  TGC  AAA  ATC  TCT  AAA  TAGGTAACCC                                        127
Cys  Asn  Cys  Lys  Ile  Ser  Lys
                35
```

( 2 ) INFORMATION FOR SEQ ID NO:5:

( i ) SEQUENCE CHARACTERISTICS:
( A ) LENGTH: 39 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Asp  Ser  Lys  Ile  Thr  Pro  Gln  Ile  Thr  Ser  Ile  Ser  Leu  Cys  Thr  Pro
 1              5                        10                       15

Gly  Cys  Val  Thr  Gly  Ala  Leu  Gln  Thr  Cys  Phe  Leu  Gln  Thr  Leu  Thr
              20                       25                       30

Cys  Asn  Cys  Lys  Ile  Ser  Lys
                35
```

( 2 ) INFORMATION FOR SEQ ID NO:6:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( x i ) SEQUENCE DESCRIPTION: SEQ ID NO:6:

TGAATTCAGA TTCGAAAATC ACTCCGCAAA TCACTAGT        38

( 2 ) INFORMATION FOR SEQ ID NO:7:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( x i ) SEQUENCE DESCRIPTION: SEQ ID NO:7:

ACCAAAGCTT CAACCCGGGT GTACAAAGTG AAATACTAGT GATTTGCGG        49

( 2 ) INFORMATION FOR SEQ ID NO:8:

( i ) SEQUENCE CHARACTERISTICS:
  ( A ) LENGTH: 144 base pairs
  ( B ) TYPE: nucleic acid
  ( C ) STRANDEDNESS: unknown
  ( D ) TOPOLOGY: linear ( i i ) MOLECULE TYPE: other nucleic acid
  ( A ) DESCRIPTION: /desc = "Synthetic DNA"

( i x ) FEATURE:
  ( A ) NAME/KEY: CDS
  ( B ) LOCATION: 1..123

( x i ) SEQUENCE DESCRIPTION: SEQ ID NO:8:

| GAT | TCG | AAA | ATC | ACT | CCG | CAA | TGG | AAA | AGT | GAA | TCA | CCT | TGT | ACA | CCC | 48 |
| Asp | Ser | Lys | Ile | Thr | Pro | Gln | Trp | Lys | Ser | Glu | Ser | Pro | Cys | Thr | Pro | |
| 40 | | | | | 45 | | | | 50 | | | | | | 55 | |

| GGG | TGT | AAA | ACC | GGC | GCC | CTG | ATG | GGT | TGT | AAC | ATG | AAA | ACA | GCC | ACG | 96 |
| Gly | Cys | Lys | Thr | Gly | Ala | Leu | Met | Gly | Cys | Asn | Met | Lys | Thr | Ala | Thr | |
| | | | | 60 | | | | | 65 | | | | | 70 | | |

| TGT | CAT | TGT | AGT | ATT | CAC | GTA | AGC | AAA | TAGGTAACCA | AATAGGTAAC | 143 |
| Cys | His | Cys | Ser | Ile | His | Val | Ser | Lys | | | |
| | | | 75 | | | | | 80 | | | |

C                                                                                                                144

( 2 ) INFORMATION FOR SEQ ID NO:9:

( i ) SEQUENCE CHARACTERISTICS:
    ( A ) LENGTH: 41 amino acids
    ( B ) TYPE: amino acid
    ( D ) TOPOLOGY: linear ( i i ) MOLECULE TYPE: protein ( x i ) SEQUENCE DESCRIPTION: SEQ ID NO:9:

| Asp | Ser | Lys | Ile | Thr | Pro | Gln | Trp | Lys | Ser | Glu | Ser | Pro | Cys | Thr | Pro |
| 1 | | | | 5 | | | | | 10 | | | | | 15 | |

| Gly | Cys | Lys | Thr | Gly | Ala | Leu | Met | Gly | Cys | Asn | Met | Lys | Thr | Ala | Thr |
| | | | | 20 | | | | | 25 | | | | | 30 | |

| Cys | His | Cys | Ser | Ile | His | Val | Ser | Lys |
| | | | 35 | | | | | 40 |

( 2 ) INFORMATION FOR SEQ ID NO:10:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( x i ) SEQUENCE DESCRIPTION: SEQ ID NO:10:

GAGAATTCTA TCCCGGGTGT AAAACCGGCG CCCTG                                                                         35

( 2 ) INFORMATION FOR SEQ ID NO:11:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( x i ) SEQUENCE DESCRIPTION: SEQ ID NO:11:

```
ATGGGTTGTA  ACATGAAAAC  AGCCACGTGT  CATTGT                                           3 6
```

( 2 ) INFORMATION FOR SEQ ID NO:12:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "Synthetic DNA"

( x i ) SEQUENCE DESCRIPTION: SEQ ID NO:12:

```
GTGAAAGCTT  GGGGTTACCT  ATTTGCTTAC  GTGAATACTA  CAATGACACG  TGGC               5 4
```